(12) United States Patent
Collins et al.

(10) Patent No.: US 7,029,854 B2
(45) Date of Patent: Apr. 18, 2006

(54) METHODS DESIGNING MULTIPLE MRNA TRANSCRIPT NUCLEIC ACID PROBE SEQUENCES FOR USE IN NUCLEIC ACID ARRAYS

(75) Inventors: Patrick J. Collins, Daly City, CA (US); Keith C. Butler, Newark, DE (US); Peter G. Webb, Menlo Park, CA (US); Karen W. Shannon, Los Gatos, CA (US); Sandra L. Tang, Saratoga, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 25 days.

(21) Appl. No.: 10/303,151

(22) Filed: Nov. 22, 2002

(65) Prior Publication Data
US 2004/0101845 A1    May 27, 2004

(51) Int. Cl.
*C12Q 1/68* (2006.01)
(52) U.S. Cl. .......................... 435/6; 435/91.1; 702/20; 536/24.3
(58) Field of Classification Search .................. 435/6, 435/91.1, 91.2; 702/19, 20
See application file for complete search history.

(56) References Cited

U.S. PATENT DOCUMENTS

| 4,433,140 | A | * | 2/1984 | Seliger et al. ........... 536/24.33 |
| 5,556,749 | A | | 9/1996 | Mitsuhashi et al. ............. 435/6 |
| 6,162,601 | A | * | 12/2000 | Bandman et al. .............. 435/6 |
| 6,251,588 | B1 | | 6/2001 | Shannon et al. ................ 435/6 |

OTHER PUBLICATIONS

Divoky et al, Gene 247(1-2), 111 (2000).*

* cited by examiner

*Primary Examiner*—James Martinell

(57) ABSTRACT

Methods of identifying a sequence of a nucleic acid that is suitable for use as a surface immobilized probe for two or more mRNA transcripts encoded by the same gene are provided. In practicing the subject methods, a consensus region for the two or more transcripts is first identified, and this identified consensus region is then employed to identify the suitable nucleic acid sequence, e.g., by using a probe design protocol. The subject invention also includes algorithms for performing the subject methods recorded on a computer readable medium, as well as computational analysis systems that include the same. Also provided are nucleic acid arrays produced with probes having sequences identified by the subject methods, as well as methods for using the same.

19 Claims, 1 Drawing Sheet

FIGURE 1

Select at least one consensus sequence for two or more different mRNA transcripts Design Probe to the Selected Consensus Sequence

METHODS DESIGNING MULTIPLE MRNA TRANSCRIPT NUCLEIC ACID PROBE SEQUENCES FOR USE IN NUCLEIC ACID ARRAYS

FIELD OF THE INVENTION

The field of this invention is nucleic acid arrays, and particularly nucleic acid probe design.

BACKGROUND OF THE INVENTION

Arrays of binding agents or probes, such as polypeptide and nucleic acids, have become an increasingly important tool in the biotechnology industry and related fields. These binding agent arrays, in which a plurality of probes are positioned on a solid support surface in the form of an array or pattern, find use in a variety of different fields, e.g., genomics (in sequencing by hybridization, SNP detection, differential gene expression analysis, identification of novel genes, gene mapping, finger printing, etc.) and proteomics.

In using such arrays, the surface bound probes are contacted with molecules or analytes of interest, i.e., targets, in a sample. Targets in the sample bind to the complementary probes on the substrate to form a binding complex. The pattern of binding of the targets to the probe features or spots on the substrate produces a pattern on the surface of the substrate and provides desired information about the sample. In most instances, the targets are labeled with a detectable label or reporter such as a fluorescent label, chemiluminescent label or radioactive label. The resultant binding interaction or complexes of binding pairs are then detected and read or interrogated, for example by optical means, although other methods may also be used depending on the detectable label employed. For example, laser light may be used to excite fluorescent labels bound to a target, generating a signal only in those spots on the substrate that have a target, and thus a fluorescent label, bound to a probe molecule. This pattern may then be digitally scanned for computer analysis.

Generally, in discovering or designing probes to be used in an array, a nucleic acid sequence is selected based on the particular gene of interest, where the nucleic acid sequence may be as great as about 60 or more nucleotides in length or as small as about 25 nucleotides in length or less. From the nucleic acid sequence, probes are synthesized according to various nucleic acid sequence regions, i.e., subsequences, of the nucleic acid sequence and are associated with a substrate to produce a nucleic acid array. As described above, a detectably labeled sample is contacted with the array, where targets in the sample bind to complimentary probe sequences of the array.

As is apparent, a key step in designing arrays is the selection of a specific probe or mixture of probes that may be used in the array and which maximize the chances of binding with target in a sample. A number of probe design protocols have been developed. For example, probe design may be performed experimentally or computationally.

When designing a genome scanning microarray, it is desirable to provide probes to all transcripts (mRNA sequences) known to occur in the organism in question. There are typically several alternative transcripts produced for each gene; such transcripts typically differ by the inclusion or exclusion of one or more exons, and by the position of the poly-adenylation site (which effectively changes the length of the 3' most exon). When multiple transcripts are present, it can be difficult to find unique probes for each transcript, particularly with the additional constraints imposed by the need to select for sensitivity and specificity.

There is a need, therefore for the development of probe design protocols that allow one to design a single probe to hybridize to all the alternative transcripts, or at least a portion of the alternative transcripts, for a gene.

Relevant Literature

U.S. patents of interest include: U.S. Pat. Nos. 6,251,588 and 5,556,749. Also of interest is Hosaka et al., Genome Informatics (2001) 12: 449–450.

SUMMARY OF THE INVENTION

Methods of identifying a sequence of a nucleic acid that is suitable for use as a surface immobilized probe for two or more mRNA transcripts encoded by the same gene are provided. In practicing the subject methods, a consensus region for the two or more transcripts is first identified, and this identified consensus region is then employed to identify the suitable nucleic acid sequence, e.g., by using a probe design protocol. The subject invention also includes algorithms for performing the subject methods recorded on a computer readable medium, as well as computational analysis systems that include the same. Also provided are nucleic acid arrays produced with probes having sequences identified by the subject methods, as well as methods for using the same.

BRIEF DESCRIPTIONS OF THE DRAWING

FIG. 1 shows a flowchart representing the steps of the subject methods.

DEFINITIONS

In the present application, unless a contrary intention appears, the following terms refer to the indicated characteristics.

The term "polymer" means any compound that is made up of two or more monomeric units covalently bonded to each other, where the monomeric units may be the same or different, such that the polymer may be a homopolymer or a heteropolymer. Representative polymers include peptides, polysaccharides, nucleic acids and the like, where the polymers may be naturally occurring or synthetic.

The term "biopolymer" refers to a polymer of one or more types of repeating units. Biopolymers are typically found in biological systems and particularly include polysaccharides (such as carbohydrates), and peptides (which term is used to include polypeptides and proteins) and polynucleotides as well as their analogs such as those compounds composed of or containing amino acid analogs or non-amino acid groups, or nucleotide analogs or non-nucleotide groups. This includes polynucleotides in which the conventional backbone has been replaced with a non-naturally occurring or synthetic backbone, and nucleic acids (or synthetic or naturally occurring analogs) in which one or more of the conventional bases has been replaced with a group (natural or synthetic) capable of participating in Watson-Crick type hydrogen bonding interactions. Polynucleotides include single or multiple stranded configurations, where one or more of the strands may or may not be completely aligned with another. For example, a "biopolymer" includes DNA (including cDNA), RNA, oligonucleotides, and PNA and other polynucleotides as described in U.S. Pat. No. 5,948, 902 and references cited therein (all of which are incorporated herein by reference), regardless of the source.

The term "nucleic acid" as used herein means a polymer composed of nucleotides, e.g., deoxyribonucleotides or ribonucleotides, or compounds produced synthetically (e.g. PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions.

The terms "ribonucleic acid" and "RNA" as used herein mean a polymer composed of ribonucleotides.

The terms "deoxyribonucleic acid" and "DNA" as used herein mean a polymer composed of deoxyribonucleotides.

The term "oligonucleotide" refers to a nucleotide multimer of about 10 to 100 nucleotides in length and up to 200 nucleotides in length.

The term "polynucleotide" as used herein refers to a nucleotide multimer having any number of nucleotides.

The term "biomonomer" references a single unit, which can be linked with the same or other biomonomers to form a biopolymer (for example, a single amino acid or nucleotide with two linking groups one or both of which may have removable protecting groups). A biomonomer fluid or biopolymer fluid reference a liquid containing either a biomonomer or biopolymer, respectively (typically in solution).

The term "monomer" as used herein refers to a chemical entity that can be covalently linked to one or more other such entities to form a polymer. Examples of "monomers" include nucleotides, amino acids, saccharides, peptides, other reactive organic molecules and the like. In general, the monomers used in conjunction with the present invention have first and second sites (e.g., C-termini and N-termini(for proteins), or 5' and 3' sites(for oligomers, RNA's, cDNA's, and DNA's)) suitable for binding to other like monomers by means of standard chemical reactions (e.g., condensation, nucleophilic displacement of a leaving group, or the like), and a diverse element which distinguishes a particular monomer from a different monomer of the same type (e.g., an amino acid side chain, a nucleotide base, etc.). In the art synthesis of biomolecules of this type utilize an initial substrate-bound monomer that is generally used as a building-block in a multi-step synthesis procedure to form a complete ligand, such as in the synthesis of oligonucleotides, oligopeptides, and the like.

The term "oligomer" is used herein to indicate a chemical entity that contains a plurality of monomers. As used herein, the terms "oligomer" and "polymer" are used interchangeably. Examples of oligomers and polymers include polydeoxyribonucleotides (DNA), polyribonucleotides (RNA), other polynucleotides which are C-glycosides of a purine or pyrimidine base, polypeptides (proteins), polysaccharides (starches, or polysugars), and other chemical entities that contain repeating units of like chemical structure.

The term "sample" as used herein relates to a material or mixture of materials, typically, although not necessarily, in fluid form, containing one or more targets, i.e., components or analytes of interest.

The terms "nucleoside" and "nucleotide" refer to a sub-unit of a nucleic acid and has a phosphate group, a 5 carbon sugar and a nitrogen containing base, as well as functional analogs (whether synthetic or naturally occurring) of such sub-units which in the polymer form (as a polynucleotide) can hybridize with naturally occurring polynucleotides in a sequence specific manner analogous to that of two naturally occurring polynucleotides. The terms "nucleoside" and "nucleotide" are intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like.

The terms "may" "optional" or "optionally" used herein interchangeably means that the subsequently described circumstance may or may not occur, so that the description includes instances where the circumstance occurs and instances where it does not.

The terms "probe", "probe sequence", "target probe" or "ligand" as used herein refer to a moiety made of an oligonucleotide or polynucleotide, as defined above, which contains a nucleic acid sequence complementary to a nucleic acid sequence present in a sample of interest such that the probe will specifically hybridize to the nucleic acid sequence present in the sample under appropriate conditions. The nucleic acid probes of the subject invention are typically associated with a support or substrate to provide an array of nucleic acid probes to be used in an array assay. The term "probe" or its equivalents as used herein refer to a compound that is "pre-synthesized" or obtained commercially, and then attached to the substrate or synthesized on the substrate, i.e., synthesized in situ on the substrate. The nucleic acid probes of the subject invention are produced, generated or synthesized according to probe sequences identified as suitable according to the subject invention that may or may not have been further tested or characterized.

The terms "reporter", "label" "detectable reporter" and "detectable label" are used herein to refer to a molecule capable of detection, including, but not limited to, radioactive isotopes, fluorescers, chemiluminescers, enzymes, enzyme substrates, enzyme cofactors, enzyme inhibitors, dyes, metal ions, metal sols, other suitable detectable markers such as biotin or haptens and the like. The term "fluorescer" refers to a substance or portion thereof which is capable of exhibiting fluorescence in the detectable range. The term "cofactor" is used broadly herein to include any molecular moiety that participates in an enzymatic reaction. Particular example of labels which may be used under the invention include, but are not limited to, fluorescein, 5(6)-carboxyfluorescein, Cyanine 3 (Cy3), Cyanine 5 (Cy5), rhodamine, dansyl, umbelliferone, Texas red, luminal, NADPH, horseradish peroxidase and $\alpha,\beta$-galactosidase.

An "array," includes any two-dimensional or substantially two-dimensional (as well as a three-dimensional) arrangement of addressable regions bearing a particular chemical moiety or moieties (e.g., biopolymers such as polynucleotide or oligonucleotide sequences (nucleic acids), polypeptides (e.g., proteins), carbohydrates, lipids, etc.) associated with that region. In the broadest sense, the preferred arrays are arrays of polymeric binding agents, where the polymeric binding agents may be any of: polypeptides, proteins, nucleic acids, polysaccharides, synthetic mimetics of such biopolymeric binding agents, etc. In many embodiments of interest, the arrays are arrays of nucleic acids, including oligonucleotides, polynucleotides, cDNAs, mRNAs, synthetic mimetics thereof, and the like. Where the arrays are arrays of nucleic acids, the nucleic acids may be covalently attached to the arrays at any point along the nucleic acid chain, but are generally attached at one of their termini (e.g. the 3' or 5' terminus). Sometimes, the arrays are arrays of polypeptides, e.g., proteins or fragments thereof.

Any given substrate may carry one, two, four or more or more arrays disposed on a front surface of the substrate. Depending upon the use, any or all of the arrays may be the same or different from one another and each may contain multiple spots or features. A typical array may contain more than ten, more than one hundred, more than one thousand more ten thousand features, or even more than one hundred thousand features, in an area of less than 20 cm² or even less than 10 cm². For example, features may have widths (that is, diameter, for a round spot) in the range from a 10 μm to 1.0 cm. In other embodiments each feature may have a width in the range of 1.0 μm to 1.0 mm, usually 5.0 μm to 500 μm, and more usually 10 μm to 200 μm. Non-round features may have area ranges equivalent to that of circular features with the foregoing width (diameter) ranges. At least some, or all, of the features are of different compositions (for example, when any repeats of each feature composition are excluded the remaining features may account for at least 5%, 10%, or 20% of the total number of features). Interfeature areas will typically (but not essentially) be present which do not carry any polynucleotide (or other biopolymer or chemical moiety of a type of which the features are composed). Such interfeature areas typically will be present where the arrays are formed by processes involving drop deposition of reagents but may not be present when, for example, photolithographic array fabrication processes are used. It will be appreciated though, that the interfeature areas, when present, could be of various sizes and configurations.

Each array may cover an area of less than 100 cm², or even less than 50 cm², 10 cm² or 1 cm². In many embodiments, the substrate carrying the one or more arrays will be shaped generally as a rectangular solid (although other shapes are possible), having a length of more than 4 mm and less than 1 m, usually more than 4 mm and less than 600 mm, more usually less than 400 mm; a width of more than 4 mm and less than 1 m, usually less than 500 mm and more usually less than 400 mm; and a thickness of more than 0.01 mm and less than 5.0 mm, usually more than 0.1 mm and less than 2 mm and more usually more than 0.2 mm and less than 1 mm. With arrays that are read by detecting fluorescence, the substrate may be of a material that emits low fluorescence upon illumination with the excitation light. Additionally in this situation, the substrate may be relatively transparent to reduce the absorption of the incident illuminating laser light and subsequent heating if the focused laser beam travels too slowly over a region. For example, substrate 10 may transmit at least 20%, or 50% (or even at least 70%, 90%, or 95%), of the illuminating light incident on the front as may be measured across the entire integrated spectrum of such illuminating light or alternatively at 532 nm or 633 nm.

Arrays can be fabricated using drop deposition from pulsejets of either polynucleotide precursor units (such as monomers) in the case of in situ fabrication, or the previously obtained polynucleotide. Such methods are described in detail in, for example, the previously cited references including U.S. Pat. No. 6,242,266, U.S. Pat. No. 6,232,072, U.S. Pat. No. 6,180,351, U.S. Pat. No. 6,171,797, U.S. Pat. No. 6,323,043, U.S. patent application Ser. No. 09/302,898 filed Apr. 30, 1999 by Caren et al., and the references cited therein. These references are incorporated herein by reference. Other drop deposition methods can be used for fabrication, as previously described herein. Also, instead of drop deposition methods, photolithographic array fabrication methods may be used such as described in U.S. Pat. No. 5,599,695, U.S. Pat. No. 5,753,788, and U.S. Pat. No. 6,329,143. Interfeature areas need not be present particularly when the arrays are made by photolithographic methods as described in those patents.

An array is "addressable" when it has multiple regions of different moieties (e.g., different polynucleotide sequences) such that a region (i.e., a "feature" or "spot" of the array) at a particular predetermined location (i.e., an "address") on the array will detect a particular target or class of targets (although a feature may incidentally detect non-targets of that feature). Array features are typically, but need not be, separated by intervening spaces. In the case of an array, the "target" will be referenced as a moiety in a mobile phase (typically fluid), to be detected by probes ("target probes") which are bound to the substrate at the various regions. However, either of the "target" or "target probe" may be the one which is to be evaluated by the other (thus, either one could be an unknown mixture of polynucleotides to be evaluated by binding with the other). A "scan region" refers to a contiguous (preferably, rectangular) area in which the array spots or features of interest, as defined above, are found. The scan region is that portion of the total area illuminated from which the resulting fluorescence is detected and recorded. For the purposes of this invention, the scan region includes the entire area of the slide scanned in each pass of the lens, between the first feature of interest, and the last feature of interest, even if there exist intervening areas which lack features of interest. An "array layout" refers to one or more characteristics of the features, such as feature positioning on the substrate, one or more feature dimensions, and an indication of a moiety at a given location. "Hybridizing" and "binding", with respect to polynucleotides, are used interchangeably.

The term "stringent hybridization conditions" as used herein refers to conditions that are that are compatible to produce duplexes on an array surface between complementary binding members, i.e., between probes and complementary targets in a sample, e.g., duplexes of nucleic acid probes, such as DNA probes, and their corresponding nucleic, acid targets that are present in the sample, e.g., their corresponding mRNA analytes present in the sample. An example of stringent hybridization conditions is hybridization at, 60° C. or higher and 3×SSC (450 mM sodium, chloride/45 mM sodium citrate). Another example of stringent hybridization conditions is incubation at 42° C. in a solution containing 30% formamide, 1M NaCl, 0.5% sodium sarcosine, 50 mM MES, pH 6.5. Stringent hybridization conditions are hybridization conditions that are at least as stringent as the above representative conditions, where conditions are considered to be at least as stringent if they are at least about 80% as stringent, typically at least about 90% as stringent as the above specific stringent conditions. Other stringent hybridization conditions are known in the art and may also be employed, as appropriate.

By "remote location," it is meant a location other than the location at which the array is present and hybridization occurs. For example, a remote location could be another location (e.g., office, lab, etc.) in the same city, another location in a different city, another location in a different state, another location in a different country, etc. As such, when one item is indicated as being "remote" from another, what is meant is that the two items are at least in different rooms or different buildings, and may be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. An array "package" may be the array plus only a substrate on which the array is deposited, although the package may include other features (such as a housing with a chamber). A "chamber" references an enclosed volume (although a chamber may be accessible through one or more ports). It will also be appreciated that throughout the present application, that words such as "top," "upper," and "lower" are used in a relative sense only.

A "computer-based system" refers to the hardware means, software means, and data storage means used to analyze the information of the present invention The minimum hardware of the computer-based systems of the present invention comprises a central processing unit (CPU), input means, output means, and data storage means. A skilled artisan can readily appreciate that any one of the currently available computer-based system are suitable for use in the present invention. The data storage means may comprise any manufacture comprising a recording of the present information as described above, or a memory access means that can access such a manufacture.

To "record" data, programming or other information on a computer readable medium refers to a process for storing information, using any such methods as known in the art. Any convenient data storage structure may be chosen, based on the means used to access the stored information. A variety of data processor programs and formats can be used for storage, e.g. word processing text file, database format, etc.

A "processor" references any hardware and/or software combination that will perform the functions required of it. For example, any processor herein may be a programmable digital microprocessor such as available in the form of a electronic controller, mainframe, server or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic medium or optical disk may carry the programming, and can be read by a suitable reader communicating with each processor at its corresponding station.

The term "gene" means the open reading frame of a genomic domain encoding specific proteins and polypeptides, and introns that are present in the open reading frame, as well as adjacent 5' and 3' non-coding nucleotide sequences involved, e.g., untranslated regions, promoter or other regulatory elements, etc., in the regulation of expression, up to about 20 kb beyond the coding region, but possibly further in either direction.

DETAILED DESCRIPTION OF THE INVENTION

Methods of identifying a sequence of a nucleic acid that is suitable for use as a surface immobilized probe for two or more mRNA transcripts encoded by the same gene are provided. In practicing the subject methods, a consensus region for the two or more transtcripts is first identified, and this identified consensus region is then employed to identify the suitable nucleic acid sequence, e.g., by using a probe design protocol. The subject invention also includes algorithms for performing the subject methods recorded on a computer readable medium, as well as computational analysis systems that include the same. Also provided are nucleic acid arrays produced with probes having sequences identified by the subject methods, as well as methods for using the same.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an" and "the" include plural reference unless the context clearly dictates otherwise. Unless defined otherwise, all technical and scientific terms used herein have the same meaning as commonly understood to one of ordinary skill in the art to which this invention belongs.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described. Methods recited herein may be carried out in any order of the recited events which is logically possible, as well as the recited order of events.

All patents and other references cited in this application, are incorporated into this application by reference except insofar as they may conflict with those of the present application (in which case the present application prevails).

In further describing the subject invention, the methods for identifying suitable probe sequences are described first in greater detail, followed by a review of arrays that may be produced using probes identified by the subject methods as well as representative applications for such arrays.

Methods

As summarized above, the subject invention provides a method of identifying or designing (i.e., determining) a sequence of a nucleic acid that is suitable for use as a substrate surface immobilized probe that can hybridize to two or more different target nucleic acids that correspond to the same genomic coding sequence. In other words, the subject invention provides a method of determining the sequence of a probe nucleic acid that can be used as a surface immobilized probe, e.g., in a nucleic acid array, for two or more mRNA transcripts that are encoded by the same gene, i.e., are transcribed from the same genomic region, e.g., of a chromosome, and arise because of an alternative splicing mechanism during the transcription step. The probes can be used for the two or more mRNA transcripts because they hybridize to the two or more mRNA transcripts, or target nucleic acids corresponding thereto, e.g., target nucleic acids that are produced therefrom, where the target nucleic acids may be DNA or RNA, as is known in the art. Because the probes identified by the subject methods can be employed for two or more mRNA transcripts encoded by the same gene, the probes have a sequence that is found in the two or more mRNA transcripts (that are transcribed from the same gene or genomic coding sequence) or the RNA/DNA complements thereof, or the DNA or RNA complements of the DNA complements. Thus, the subject methods are methods of identifying a probe sequence that can be used for at least two of the mRNA transcripts that correspond to a gene that is transcribed into multiple mRNA transcripts, where in certain embodiments the subject methods identify probe that can be used for all of the mRNA transcripts that correspond to a single gene. The number of mRNA transcripts that may be detected using the probes identified by the subject methods may range from about 2 to about 500 or more, such as from about 2 to 50, including from about 2 to about 50.

In the subject methods, the first step is to select at least one consensus sequence for two or more different mRNA transcripts that are transcribed from the same genomic coding sequence of interest. In performing this step, the sequences of all of the mRNA transcripts of interest that are transcribed from the same gene (i.e., genomic coding sequence) are first provided, e.g., from a database of such sequences. The transcripts of interest may be all of the known transcripts or a subportion thereof, for a given gene, e.g., 75, 50, 25 number %, etc. Next, at least one consensus sequence or region shared by at least some of the mRNA transcripts of interest, and preferably all of the mRNA transcripts of interest, is identified. By consensus sequence is meant a region of sequence identity, typically absolute or 100% sequence identity (e.g., as determined by manual alignment or the BLAST program, e.g., using default settings). Typically, the consensus sequences that are identified are at least about 200 nt in length, typically at least about 1,000 nt in length, such as at least about 2,000 nt in length, where the identified consensus sequences may be as long as 82,000 nt in length or longer, such as at least about 6,000 nt in length or longer, where in many embodiments the length of the consensus sequences identified in this step of the subject methods ranges from about 200 nt to about 6,000 nt, such as from about 1,000 nt to about 2,000 nt.

As indicated above, the first step of the subject methods is a consensus sequence identification step, where at least one consensus sequence or region is identified. The number of consensus sequences identified may vary, but is often from about 1 to about 5, such as from about 1 to about 3. In addition, depending on the nature of the transcripts of interest, a consensus sequence may not be identified. In this situation, probes are designed for the transcripts using an alternative protocol, as reviewed in greater detail below.

The consensus sequence may be identified using any convenient protocol, such as aligning all of the sequences of the mRNA transcripts and scanning the aligned sequences for regions of sequence identity, e.g., using any of the numerous alignment algorithms available and well known to those of skill in the art, e.g., BLAST (described in Altschul et al. (1990); *J. Mol. Biol.* 215:403–10), etc.

In one particular consensus sequence identification protocol of interest, the consensus sequence identification protocol lines all the exons appearing in the mRNA transcripts of interest up along the genomic sequence of interest and identifies regions of the genome as consensus sequences if the regions include any exon (or portion thereof) that is found in all of the mRNA transcripts of interest. In other words, where an exon (or portion thereof) appearing in each of the transcripts of interest overlaps in the genomic sequence, the region of the genomic sequence that includes that exon (or portion thereof) is identified as a consensus sequence or region. As is apparent, using this procedure, multiple consensus sequences or regions may be identified in the genomic sequence that encodes the two or more transcripts of interest. In certain embodiments, two adjacent but separate genomic regions may be identified, where the adjacent but separate regions are not separated by a third exon that is not common to all of the transcripts of interest. In such a situation, the consensus sequence identification protocol may merge the two regions into a single region, also called a merged consensus region or just a consensus region.

The above first step of the subject methods results in the identification of at least one consensus sequence or region for those transcripts of interest that include such a region. The at least one consensus sequence is then employed in the second step to design a probe for the consensus sequence. Where multiple consensus sequences are identified in the first step of the subject methods, often only one of the multiply identified consensus sequences will be selected or chosen for use in the probe design step of the subject methods. In many such embodiments, the consensus sequence that is chosen from the multiple candidate consensus sequences is the one that is the most 3' of the consensus sequences, i.e., the one that lies in the most 3' position of the corresponding transcripts. In many embodiments, if the 3'-most region is not greater than a certain size (e.g. 400 bases) then a region further from the 3' end can be chosen if it meets other criteria (e.g., is greater than a certain size and still within 1200 bases of the 3' end.)

Depending on the initial sequence information database employed in the subject methods, the consensus sequence identification protocol or method may be adjusted to account for sequence disparities or other database specific features, such as width variance, etc., where representative database disparities and approaches to accommodate the same, are further described in the experimental section, below.

Once the consensus sequence is identified, at least one probe sequence is designed from the previously selected consensus sequence or region. Any convenient probe design protocol or approach may be employed, where a number of such protocols are already known and employed by those of skill in the art. In certain embodiments, computational or "in silico" probe design protocols are of interest, where such protocols typically examine a target sequence (in this case the consensus sequence) and identify probe sequences based on one or more criteria of interest. Representative criteria that are employed in such probe design approaches include, but are not limited to: distance from 3' end, base content (e.g., GC base content), propensity for cross-hybridization, e.g., with other sequences likely to be encountered during use, secondary structure formation, etc. Where propensity for cross-hybridization is one of the criteria employed, a database of all known transcripts for the organism, including each of the multiple transcripts for which the consensus sequence was identified, may be employed.

Numerous different probe design protocols are known, where representative protocols that may be of interest include but are not limited to: the probe design protocols described in U.S. Pat. Nos 6,251,588 and 5,556,749; the disclosures of which are herein incorporated by reference. Also of interest is the probe design protocol described in U.S. application Ser. No. 10/184,501 titled "Method for Identifying Suitable Nucleic Acid Probe Sequences for Use in Nucleic Acid Arrays," and filed on Jun. 26, 2002; the disclosure of which is herein incorporated by reference.

In certain embodiments of interest, the probe design protocol described in U.S. application Ser. No. 10/303,160 titled "Methods for Identifying Suitable Nucleic Acid Probe Sequences for Use in Nucleic Acid Arrays," and filed on even date herewith (the disclosure of which is herein incorporated by reference) is employed in this step of the subject methods. The probes identified using this particular probe design method are suitable for use as array probes because they exhibit similar functional properties under a variety of different experimental conditions, e.g., differential gene expression assays. A feature of the this particular probe design method is that it includes both computational steps and empirical steps, where specifically a collection of candidate probe sequences for a given target nucleic acid (which is the previously identified and selected consensus sequence) are first computationally identified from the sequence of the target nucleic acid of interest, where the initially identified candidate sequences are subsequently tested empirically and then further evaluated using additional computational steps in order to identify a suitable probe sequence.

In many of these embodiments, the probe design protocol employed includes the following steps: (a) identifying a plurality of candidate probe sequences for the target nucleic acid; (b) empirically evaluating each of the identified candidate probe sequences; (c) clustering the identified candidate probe sequences into two or more groups of candidate probe sequences based observed empirical data values; (d) selecting one of the two or more groups of candidate probe sequences as the "best" group; and (e) choosing a candidate probe sequence from the selected "best" group as the sequence that is suitable for use in a probe for the target nucleic acid of interest.

Each of these steps is further described in copending U.S. application Ser. No. 10/303,160 titled "Methods for Identifying Suitable Nucleic Acid Probe Sequences for Use in Nucleic Acid Arrays," and filed on even date herewith (the disclosure of which is herein incorporated by reference)

In many embodiments, the probe nucleic acid sequences identified using the subject methods are provided in text format or as a string of text, where the text represents or corresponds to the sequence of nucleotides of a probe nucleic acid. The nucleic acid sequences can be of any length, where the nucleic acid sequences are typically about 20 nt to about 100 nt in length, e.g., from about 20 to about 80 nt in length, e.g., 25 nt, 60 nt, etc. However, nucleic acid sequences of lesser or greater length may be identified as appropriate. Suitable nucleic acid probes produced therefrom may be oligonucleotides or polynucleotides, as will be described in greater detail below. A feature of the sequences identified according to the methods described above is that they can be employed in probes which can detect two or more different transcripts transcribed from the same gene, as described above, where in certain embodiments the probes that include sequences identified according to the subject methods are capable of be used for all of the transcripts of a given gene.

One or more aspects of the above methodology may be in the form of computer readable media having programming stored thereon for implementing the subject methods. In other words, the subject methodology may be provided in the form of programming or an algorithm recorded onto a computer readable medium. The computer readable media may be, for example, in the form of a computer disk or CD, a floppy disc, a magnetic "hard card", a server, or any other computer readable media capable of containing data or the like, stored electronically, magnetically, optically or by other means. Accordingly, stored programming embodying steps for carrying-out the subject methods may be transferred to a computer such as a personal computer (PC), (i.e., accessible by a researcher or the like), by physical transfer of a CD, floppy disk, or like medium, or may be transferred using a computer network, server, or other interface connection, e.g., the Internet.

In certain embodiments, the programming or algorithm may perform one or more additional optional features. For example, the programming may be adaptable for use with transcripts for which no consensus sequence can be determined. In such embodiments, the programming may employ a representative transcript sequence as the target sequence in the subsequent probe design method, where the representative transcript sequence may be selected from a population of transcripts based on one or more criteria, e.g., relative abundance, etc. The programming may also be adaptable for use with single transcript genes, where the programming merely skips the consensus region identification step and uses the sequence of the single transcript gene as the target sequence in the subsequent probe design step.

In one embodiment of the subject invention, a system of the invention may include a single computer or the like with a stored algorithm capable of carrying out suitable probe identification methods, i.e., a computational analysis system. In certain embodiments, the system is further characterized in that it provides a user interface, where the user interface presents to a user the option of selecting among one or more different, including multiple different, inputs, e.g., e.g., various parameter values for the algorithm, as described above, such, as consensus sequence identification parameters, like consensus sequence width, distance from 3' end, etc. Computational systems that may be readily modified to become systems of the subject invention include those described in U.S. Pat. No. 6,251,588; the disclosure of which is herein incorporated by reference.

Utility

The above-described methods and devices programmed to practice the same may be used to identify probe nucleic acids to be produced on surfaces of any of a variety of different substrates, including both flexible and rigid substrates, e.g., in the production of nucleic acid arrays. Preferred materials provide physical support for the deposited material and endure the conditions of the deposition process and of any subsequent treatment or handling or processing that may be encountered in the use of the particular array. The array substrate may take any of a variety of configurations ranging from simple to complex. Thus, the substrate could have generally planar form, as for example, a slide or plate configuration, such as a rectangular or square disc. In many embodiments, the substrate will be shaped generally as a rectangular solid, having a length in the range of about 4 mm to 200 mm, usually about 4 mm to 150 mm, more usually about 4 mm to 125 mm; a width in the range of about 4 mm to 200 mm, usually about 4 mm to 120 mm, and more usually about 4 mm to about 80 mm; and a thickness in the range of about 0.01 mm to about 5 mm, usually from about 0.1 mm to about 2 mm and more usually from about 0.2 mm to about 1 mm. However, larger or smaller substrates may be and can be used, particularly when such are cut after fabrication into smaller size substrates carrying a smaller total number of arrays 12. Substrates of other configurations and equivalent areas can be chosen. The configuration of the array may be selected according to manufacturing, handling, and use considerations.

The substrates may be fabricated from any of a variety of materials. In certain embodiments, such as for example where production of binding pair arrays for use in research and related applications is desired, the materials from which the substrate may be fabricated should ideally exhibit a low level of non-specific binding during hybridization events. In many situations, it will also be preferable to employ a material that is transparent to visible and/or UV light. For flexible substrates, materials of interest include: nylon, both modified and unmodified, nitrocellulose, polypropylene, and the like, where a nylon membrane, as well as derivatives thereof, may be particularly useful in this embodiment. For rigid substrates, specific materials of interest include: glass; fuse silica; silicon, plastics (for example polytetraflouroethylene, polypropylene, polystyrene, polycarbonate, and blends thereof, and the like); metals (for example, gold, platinum, and the like).

The substrate surface onto which the polynucleotide compositions or other moieties are deposited may be smooth or substantially planar, or have irregularities, such as depressions or elevations. The surface may be modified with one or more different layers of compounds that serve to modify the properties of the surface in a desirable manner. Such modification layers of interest include: inorganic and organic layers such as metals, metal oxides, polymers, small organic molecules and the like. Polymeric layers of interest include layers of: peptides, proteins, polynucleic acids or mimetics thereof (for example, peptide nucleic acids and the like); polysaccharides, phospholipids, polyurethanes, polyesters, polycarbonates, polyureas, polyamides, polyetheyleneamines, polyarylene sulfides, polysiloxanes, polyimides, polyacetates, and the like, where the polymers may be heteroor homopolymeric, and may or may not have separate functional moieties attached thereto (for example, conjugated).

Arrays

Also provided by the subject invention are novel nucleic acid arrays of produced using the subject methods, as described above. The subject arrays include at least one probe, and typically a plurality of different probes of different sequence (e.g., at least about 10, usually at least about 50, such as at least about 100, 1000, 5000, 10,000 or more) immobilized on, e.g., covalently or non-covalently attached to, different and known locations on the substrate surface. A feature of the subject arrays is that at least one of the probes is a probe having a sequence identified according to the present methods, where in many embodiments at least about 5, 10, 50, 100, 500, 1000, 5000, 10000 or more of the, probe sequences are sequences identified by the subject methods. Each distinct nucleic acid sequence of the array is typically present as a composition of multiple copies of the polymer on the substrate surface, e.g., as a spot on the surface of the substrate. The number of distinct nucleic acid sequences, and hence spots or similar structures (i.e., array features), present on the array may vary, but is generally at least 2, usually at least 5 and more usually at least 10, where the number of different spots on the array may be as a high as 50, 100, 500, 1000, 10,000 or higher, depending on the intended use of the array. The spots of distinct nucleic acids present on the array surface are generally present as a pattern, where the pattern may be in the form of organized rows and columns of spots, e.g., a grid of spots, across the substrate surface, a series of curvilinear rows across the substrate surface, e.g., a series of concentric circles or semi-circles of spots, and the like. The density of spots present on the array surface may vary, but will generally be at least about 10 and usually at least about 100 spots/cm$^2$, where the density may be as high as $10^6$ or higher, but will generally not exceed about $10^5$ spots/cm$^2$. In the subject arrays of nucleic acids, the nucleic acids may be covalently attached to the arrays at any point along the nucleic acid chain, but are generally attached at one of their termini, e.g., the 3' or 5' terminus.

A feature of the subject arrays is that they include one or more, usually a plurality of, probes whose sequence has been selected according to the subject protocols. Because the sequences of the probes on the arrays are selected according to the above protocols, the probe sequences are ones that can detect two or more different transcripts of a single gene, e.g., all of the transcripts of a single gene, in the sample. In many embodiments, at least about 25 number %, such as at least about 50 number %, 75 number % or more, e.g., 90, 95 or 99 or more, up to an including 100 number %, of the probes of the array are probes identified by the subject methods.

Utility of Arrays

The subject arrays find use in a variety applications, where such applications are generally analyte detection applications in which the presence of a particular analyte in a given sample is detected at least qualitatively, if not quantitatively. Protocols for carrying out such assays are well known to those of skill in the art and need not be described in great detail here. Generally, the sample suspected of comprising the analyte of interest is contacted with an array produced according to the subject methods under conditions sufficient for the analyte to bind to its respective binding pair member that is present on the array. Thus, if the analyte of interest is present in the sample, it binds to the array at the site of its complementary binding member and a complex is formed on the array surface. The presence of this binding complex on the array surface is then detected, e.g., through use of a signal production system, e.g., an isotopic or fluorescent label present on the analyte, etc. The presence of the analyte in the sample is then deduced from the detection of binding complexes on the substrate surface.

Specific analyte detection applications of interest include hybridization assays in which the nucleic acid arrays of the subject invention are employed. In these assays, a sample of target nucleic acids is first prepared, where preparation may include labeling of the target nucleic acids with a label, e.g., a member of signal producing system. Where the arrays include "all-bases-all-layers" control probes, as described above, a collection of labeled control targets is typically included in the sample, where the collection may be made up of control targets that are all labeled with the same label or two or more sets that are distinguishably labeled with different labels, as described above. Following sample preparation, the sample is contacted with the array under hybridization conditions, whereby complexes are formed between target nucleic acids that are complementary to probe sequences attached to the array surface. The presence of hybridized complexes is then detected. Specific hybridization assays of interest which may be practiced using the subject arrays include: gene discovery assays, differential gene expression analysis assays; nucleic acid sequencing assays, and the like. Patents and patent applications describing methods of using arrays in various applications include: U.S. Pat. Nos. 5,143,854; 5,288,644; 5,324,633; 5,432,049; 5,470,710; 5,492,806; 5,503,980; 5,510,270; 5,525,464;

5,547,839; 5,580,732; 5,661,028; 5,800,992; the disclosures of which are herein incorporated by reference.

In certain embodiments, the subject methods include a step of transmitting data from at least one of the detecting and deriving steps, as described above, to a remote location. By "remote location" is meant a location other than the location at which the array is present and hybridization occur. For example, a remote location could be another location (e.g., office, lab, etc.) in the same city, another location in a different city, another location in a different state, another, location in a different country; etc. As such, when one item is indicated as being "remote" from another, what is meant is that the two items are at least in different buildings, and may be at least one mile, ten miles, or at least one hundred miles apart. "Communicating" information means transmitting the data representing that information as electrical signals over a suitable communication channel (for example, a private or public network). "Forwarding" an item refers to any means of getting that item from one location to the next, whether by physically transporting that item or otherwise (where that is possible) and includes, at least in the case of data, physically transporting a medium carrying the data or communicating the data. The data may be transmitted to the remote location for further evaluation and/or use. Any convenient telecommunications means may be employed for transmitting the data, e.g., facsimile, modem, internet, etc.

As such, in using an array made by the method of the present invention, the array will typically be exposed to a sample (for example, a fluorescently labeled analyte, e.g., protein containing sample) and the array then read. Reading of the array may be accomplished by illuminating the array and reading the location and intensity of resulting fluorescence at each feature of the array to detect any binding complexes on the surface of the array. For example, a scanner may be used for this purpose which is similar to the AGILENT MICROARRAY SCANNER device available from Agilent Technologies, Palo Alto, Calif. Other suitable apparatus and methods are described in U.S. Pat. Nos. 5,091,652; 5,260,578; 5,296,700; 5,324,633; 5,585,639; 5,760,951; 5,763,870; 6,084,991; 6,222,664; 6,284,465; 6,371,370 6,320,196 and 6,355,934; the disclosures of which are herein incorporated by reference. However, arrays may be read by any other method or apparatus than the foregoing, with other reading methods including other optical techniques (for example, detecting chemiluminescent or electroluminescent labels) or electrical techniques (where each feature is provided with an electrode to detect hybridization at that feature in a manner disclosed in U.S. Pat. No. 6,221,583 and elsewhere). Results from the reading may be raw results (such as fluorescence intensity readings for each feature in one or more color channels) or may be processed results such as obtained by rejecting a reading for a feature, which is below a predetermined threshold and/or forming conclusions based on the pattern read from the array (such as whether or not a particular target sequence may have been present in the sample). The results of the reading (processed or not) may be forwarded (such as by communication) to a remote location if desired; and received there for further use (such as further processing).

Kits

Kits for use in analyte detection assays are also provided. The kits at least include the arrays of the invention, as described above. The kits may further include one or more additional components necessary for carrying out an analyte detection assay, such as sample preparation reagents, buffers, labels, and the like. As such, the kits may include one or more containers such as vials or bottles, with each container containing a separate component for the assay, and reagents for carrying out an array assay such as a nucleic acid hybridization assay or the like. The kits may also include a denaturation reagent for denaturing the analyte, buffers such as hybridization buffers, wash mediums, enzyme substrates, reagents for generating a labeled target sample such as a labeled target nucleic acid sample, negative and positive controls and written instructions for using the array assay devices for carrying out an array based assay. Such kits also typically include instructions for use in practicing array based assays.

Kits for use in connection with the probe design protocols of the subject invention may also be provided. Such kits preferably include at least a computer readable medium including programming as discussed above and instructions. The instructions may include installation or setup directions. The instructions may include directions for use of the invention.

Providing software and instructions as a kit may serve a number of purposes. The combinations may be packaged and purchased as a means of upgrading an existing fabrication device. Alternatively, the combination may be provided in connection with a new device for fabricating arrays, in which the software may be preloaded on the same. In which case, the instructions will serve as a reference manual (or a part thereof) and the computer readable medium as a backup copy to the preloaded utility.

The instructions of the above-described kits are generally recorded on a suitable recording medium. For example, the instructions may be printed on a substrate, such as paper or plastic, etc. As such, the instructions may be present in the kits as a package insert, in the labeling of the container of the kit or components thereof (i.e. associated with the packaging or sub packaging), etc. In other embodiments, the instructions are present as an electronic storage data file present on a suitable computer readable storage medium, e.g., CD-ROM, diskette, etc, including the same medium on which the program is presented.

In yet other embodiments, the instructions are not themselves present in the kit, but means for obtaining the instructions from a remote source, e.g. via the Internet, are provided. An example of this embodiment is a kit that includes a web address where the instructions can be viewed and/or from which the instructions can be downloaded. Conversely, means may be provided for obtaining the subject programming from a remote source, such as by providing a web address. Still further, the kit may be one in which both the instructions and software are obtained or downloaded from a remote source, as in the Internet or World Wide Web. Some form of access security or identification protocol may be used to limit access to those entitled to use the subject invention. As with the instructions, the means for obtaining the instructions and/or programming is generally recorded on a suitable recording medium.

The following examples are offered by way of illustration and not by way of limitation.

Experimental

I. Preparation of Nucleic Acid Array Having Human-Specific Content:

Using the 17,838 sequences found in the June 2002 release of Incyte's Life Seq™ Foundation "full-length" database (available from Incyte Genomics, Palo Alto, Calif.), a human oligo array was designed using the subject probe design methods as follows:

The protocol starts by identifying certain information about every exon of every transcript (mRNA) of each gene under consideration. This information comes from the LifeSeq™ Foundation database (Incyte Genomics, Palo Alto, Calif.). Each exon's genomic start and stop address is used to determine where exons from different transcripts overlap (i.e., form consensus regions.) Each exon's cDNA start and stop address (along the transcript, not the genome) is used to determine how far that exon (and hence any consensus region) is from the 3' end of the transcript.

Exon overlap is determined in the following manner. (This could be characterized as a brute-force algorithm; many other algorithms are possible.) A one-million-number-long array (denoted as the 'overlap' array) is employed. Genomic start and stop addresses are numbers with values from 0 to 1 million. At the beginning of processing each gene, the array is initially set to contain all zeros. Then positions in the array corresponding to addresses of each nucleic acid base in an exon are incremented by 1. After processing all exons for all transcripts for the gene in this manner, any place in the array that contains a number equal to the number of transcripts in the gene, denotes a consensus region.

Exon distance from the 3' end is monitored in the following manner. An array (e.g., one that can handle integers as large as 82,000 or more) for each expected transcript (the gene in ADHOC1A with the most transcripts had 46 of them) is used. These are referred to as 'position' arrays and there is one for each expected transcript. Each position array is 1 million numbers long. Each time an entry in the 'overlap' array is incremented (because an exon of a transcript is at that position), the same position in the particular 'position' array that corresponds to that transcript is set to the position of that exon's base in that transcript (i.e. the base's cDNA address).

After processing all exons for all transcripts for the gene, the overlap array is scanned looking for consensus regions. Anywhere a consensus region is detected in the overlap array, that position in all the corresponding position arrays is scanned to find the greatest distance that base is from the end of any transcript. This information is used to determine the maximum distance that consensus region is from the 3' end of any transcript. If, between two consensus regions, no transcript has any exons (this is denoted by a continuous string of values of zero in the position array between values equal to the number of transcripts in the gene), those regions are merged into one. After all consensus regions are found, merged if possible, and max distance from 3' end is determined, that information is written to storage for later processing. Each gene can have zero or more consensus regions.

Two problems exist in the LifeSeq Foundation database that must be addressed. First, depending on whether the gene is on the DNA's sense strand or its nonsense strand, the exon's genomic starting address may be greater than or less than its genomic stopping address. The algorithm employed in this specific example was designed to detect this difference and adjust the direction it counts on the overlap and position arrays, as well as calculating the genomic width correctly.

In addition, for some exons, the reported cDNA width (defined as absolute value of cDNA starting address—cDNA stopping address) is not the same as the reported genomic width (defined as absolute value of genomic starting address—genomic stopping address.) Sometimes genomic width is greater, sometimes cDNA width is greater. The algorithm does not assume to know which width is correct. Instead, it merges regions based upon their genomic width (regardless of whether cDNA width is greater or less) but adjusts the distance from 3' end according to the lesser of genomic or cDNA width. Differences in widths in the June version of LifeSeq Foundation were 0 to 377 bases. Many other ways are possible for the algorithm (process) to handle this problem, for instance by always using the shortest width or the longest width or by calling this instance to the attention of a human and letting them decide how to handle it. Additionally, sources of data other than LifeSeq Foundation may have different problems with their data. The actual implementation of the algorithm may be modified to identify and recover from these.

After the above process identifies the starting and stopping cDNA address of consensus regions, another process uses these addresses to access a file containing nucleic acid sequences for the associated transcripts. From this it lists the actual sequences corresponding to the starting and stopping addresses. After that, those sequences are submitted to probe design but only if they match other critera; for instance they are wide enough (e.g., 400 bases or more) and close enough to the 3' end of any transcript (e.g., within 1200 bases of the 3' end.) For each gene that does not have an acceptable consensus region, the 1200 3'-most bases of the representative transcript (as identified by LifeSeq Foundation) are used instead.

It is evident from the above results and discussion that a new and useful method of designing probes for use on nucleic acid microarrays is provided by the subject invention. Benefits of using probes on arrays that are designed, according to the present methods include, but are not limited to: (1) the ability to use a single probe for all transcripts (or a least a subportion thereof) of a given gene, allowing a broad selection of probes, and thus a strong probability of designing a good probe; (2) the ability to detect as many transcripts as possible; and (3) the ability to construct a broad similarity database. As such, the subject invention represents a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of identifying a nucleic acid sequence for a substrate surface immobilized probe for two or more different mRNA transcripts encoded by the same genomic coding sequence, said method comprising:
    (a) selecting at least one consensus sequence for said two or more different mRNA transcripts that are transcribed from said same genomic coding sequence;
    (b) identifying a plurality of candidate sequences for said at least one consensus sequence; and (c) choosing a probe sequence from said plurality to identify said nucleic acid sequence for said substrate surface immobilized probe.

2. The method according to claim 1, wherein said consensus sequence is selected by identifying a genomic region that includes an exon sequence found in each of said two or more mRNA transcripts.

3. The method according to claim 1, wherein said selecting step (a) provides two or more consensus sequences and said method further comprises picking the most 3' consensus sequence from said two or more consensus sequences as the consensus sequence employed in said step (b).

4. The method according to claim 1, wherein said probe sequence for said consensus sequence is chosen using a probe design protocol.

5. The method according to claim 4, wherein said probe design protocol comprises:
   (a) identifying a plurality of candidate probe sequences for said consensus sequence using at least one selection criterion;
   (b) empirically evaluating each of said candidate probe sequences under a plurality of different experimental conditions to obtain a collection of empirical data values for each of said candidate nucleic acid probe sequences for each of said plurality of different experimental conditions;
   (c) clustering said candidate probe sequences into two or more groups of candidate probe sequences using each candidate probe sequences collection of empirical data values;
   (d) selecting one of said two or more groups using at least one criterion; and
   (e) choosing a candidate probe sequence from said selected group as said suitable nucleic acid sequence.

6. The method according to claim 1, wherein at least some of said steps are carried out by a computational analysis system.

7. A computational analysis system comprising a computer-readable medium according to claim 6.

8. A kit for identifying a sequence of a nucleic acid that is suitable for use as a substrate surface immobilized probe that can hybridize to two or more different target nucleic acids that correspond to the same genomic coding sequence, said kit comprising:
   (a) a computer readable medium according to claim 6; and
   (b) instructions for using said algorithm to identify said suitable sequence.

9. A computer-readable medium having recorded thereon a program that identifies a sequence of a nucleic acid according to the method of claim 1.

10. A method of producing a nucleic acid array, said method comprising:
    producing at least two different probe nucleic acids immobilized on a surface of a solid support, wherein at least one of said at least two different probe nucleic acids has a sequence of nucleotides identified according to the method of claim 1.

11. The method according to claim 10, wherein said at least two different probe nucleic acids are produced on said surface of said solid support by synthesizing said probe nucleic acids on said surface.

12. The method according to claim 10, wherein said at least two different probe nucleic acids are produced on said surface of said solid support by depositing said at least two different probe nucleic acids onto said surface of said solid support.

13. A nucleic acid array produced according to the method of claim 10.

14. A method of detecting the presence of a nucleic acid analyte in a sample, said method comprising:
    (a) contacting a nucleic acid array according to claim 13 having a nucleic acid probe that specifically binds to said nucleic acid analyte with a sample suspected of comprising said analyte under conditions sufficient for binding of said analyte to said nucleic acid ligand on said array to occur; and
    (b) detecting the presence of binding complexes on the surface of said array to detect the presence of said analyte in said sample.

15. The method according to claim 14, wherein said method further comprises a data transmission step in which a result from a reading of the array is transmitted from a first location to a second location.

16. The method according to claim 15, wherein said second location is a remote location.

17. A method comprising receiving a transmitted result of a reading of an array obtained according to the method claim 14.

18. The method according to claim 1, wherein said at least one consensus sequence shares 100% sequence identity with at least a portion of each of said two or more different mRNA transcripts.

19. The method according to claim 1, wherein said consensus sequence ranges from about 200 to about 6,000 nucleotides in length.

* * * * *

UNITED STATES PATENT AND TRADEMARK OFFICE
CERTIFICATE OF CORRECTION

PATENT NO.       : 7,029,854 B2                                    Page 1 of 1
APPLICATION NO.  : 10/303151
DATED            : April 18, 2006
INVENTOR(S)      : Collins et al.

It is certified that error appears in the above-identified patent and that said Letters Patent is hereby corrected as shown below:

On the title page, in item (54), in "Title", in column 1, line 1, after "METHODS" insert -- FOR --.

On the title page, in item (54), in "Title", in column 1, line 1, delete "MRNA" and insert -- mRNA --, therefor.

On the title page, in item (56), under "Other Publications", in column 2, line1, delete "Divoky et al," and insert -- Divoky et al., --, therefor.

In column 1, line 1, after "METHODS" inset -- FOR --.

In column 1, line 1, delete "MRNA" and insert -- mRNA --, therefor.

In column 19, line 29, in Claim 5, delete "sequences" and insert -- sequence's -- therefor.

Signed and Sealed this

Fifth Day of December, 2006

JON W. DUDAS
*Director of the United States Patent and Trademark Office*